(12) United States Patent
Lieberman

(10) Patent No.: US 7,749,228 B2
(45) Date of Patent: Jul. 6, 2010

(54) ARTICULATABLE APPARATUS FOR CUTTING BONE

(75) Inventor: Isador H. Lieberman, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 10/540,380

(22) PCT Filed: Dec. 23, 2003

(86) PCT No.: PCT/US03/41044

§ 371 (c)(1),
(2), (4) Date: Jun. 23, 2005

(87) PCT Pub. No.: WO2004/060175

PCT Pub. Date: Jul. 22, 2004

(65) Prior Publication Data

US 2006/0074427 A1  Apr. 6, 2006

Related U.S. Application Data

(60) Provisional application No. 60/436,867, filed on Dec. 27, 2002.

(51) Int. Cl.
*A61B 17/00* (2006.01)

(52) U.S. Cl. .................................................. 606/84

(58) Field of Classification Search ............... 606/79, 606/80, 81; 604/528; 30/167, 167.2, 168, 30/358, 362; 175/426

See application file for complete search history.

(56) References Cited

U.S. PATENT DOCUMENTS

| 1,589,508 | A | * | 6/1926 | Boynton | 175/267 |
| 1,607,662 | A | * | 11/1926 | Boynton | 175/228 |
| 1,750,953 | A | * | 3/1930 | Boynton | 175/267 |
| 2,100,319 | A | * | 11/1937 | Brown et al. | 433/122 |
| 2,877,986 | A | * | 3/1959 | Clavier et al. | 175/319 |
| 3,609,864 | A | * | 10/1971 | Bassett | 30/261 |
| 4,788,976 | A | * | 12/1988 | Dee | 606/167 |
| 4,880,015 | A | * | 11/1989 | Nierman | 600/564 |

(Continued)

*Primary Examiner*—Thomas C Barrett
*Assistant Examiner*—Nicholas Woodall
(74) *Attorney, Agent, or Firm*—Tarolli, Sundheim, Covell & Tummino LLP

(57) ABSTRACT

An apparatus for cutting bone is provided, the apparatus includes an elongate member having a central axis. The elongate member includes a tubular portion that extends between a proximal end portion and a distal end portion. The distal end portion includes an articulatable head section with a stop surface and a cutting edge projecting from the stop surface. The head section is articulatable about a pivot axis that extends transverse to the central axis. The apparatus further includes a mechanism for articulating the head section relative to the tubular portion.

15 Claims, 4 Drawing Sheets

U.S. PATENT DOCUMENTS

| | | |
|---|---|---|
| 4,969,888 A | 11/1990 | Scholten et al. |
| 5,108,404 A | 4/1992 | Scholten et al. |
| 5,135,528 A | 8/1992 | Winston |
| 5,372,587 A * | 12/1994 | Hammerslag et al. .... 604/95.04 |
| 5,431,671 A * | 7/1995 | Nallakrishnan ............. 606/167 |
| 5,549,637 A * | 8/1996 | Crainich ..................... 606/207 |
| 5,702,408 A | 12/1997 | Wales et al. |
| 5,836,958 A | 11/1998 | Ralph |
| 5,871,204 A * | 2/1999 | Spirer ...................... 254/26 R |
| 5,928,239 A | 7/1999 | Mirza |
| 6,309,403 B1 * | 10/2001 | Minor et al. ................. 606/205 |
| 6,440,138 B1 | 8/2002 | Reiley et al. |
| 6,582,432 B1 * | 6/2003 | Michelson ................... 606/61 |
| 6,635,060 B2 | 10/2003 | Hanson et al. |
| 6,830,574 B2 * | 12/2004 | Heckele et al. .............. 606/104 |
| 6,918,914 B2 * | 7/2005 | Bauer .......................... 606/81 |
| 2001/0034526 A1 * | 10/2001 | Kuslich et al. ................ 606/80 |
| 2002/0032447 A1 * | 3/2002 | Weikel et al. ................. 606/86 |
| 2003/0212402 A1 * | 11/2003 | White et al. .................. 606/81 |
| 2004/0092933 A1 * | 5/2004 | Shaolian et al. .............. 606/61 |
| 2005/0216020 A1 * | 9/2005 | Orton .......................... 606/80 |
| 2006/0189994 A1 * | 8/2006 | Wolford et al. .............. 606/80 |

\* cited by examiner

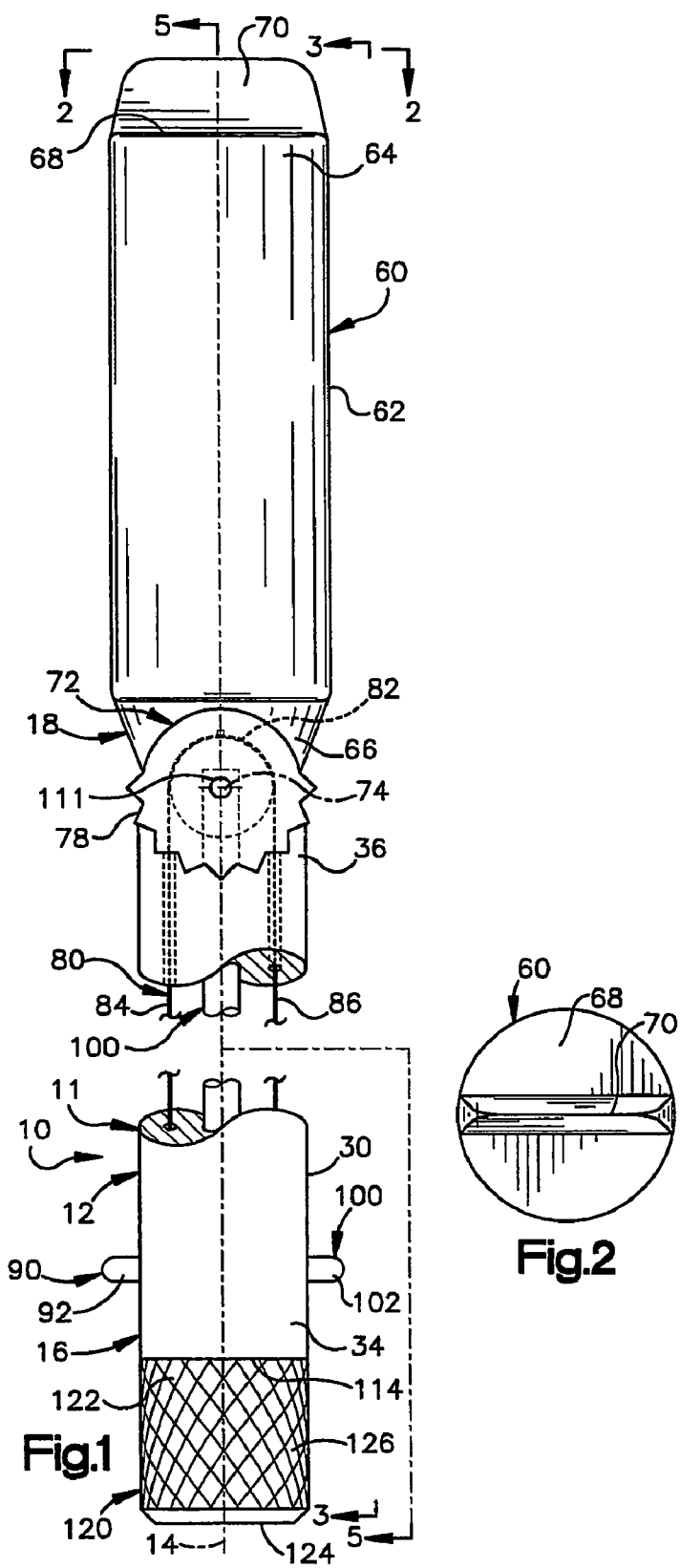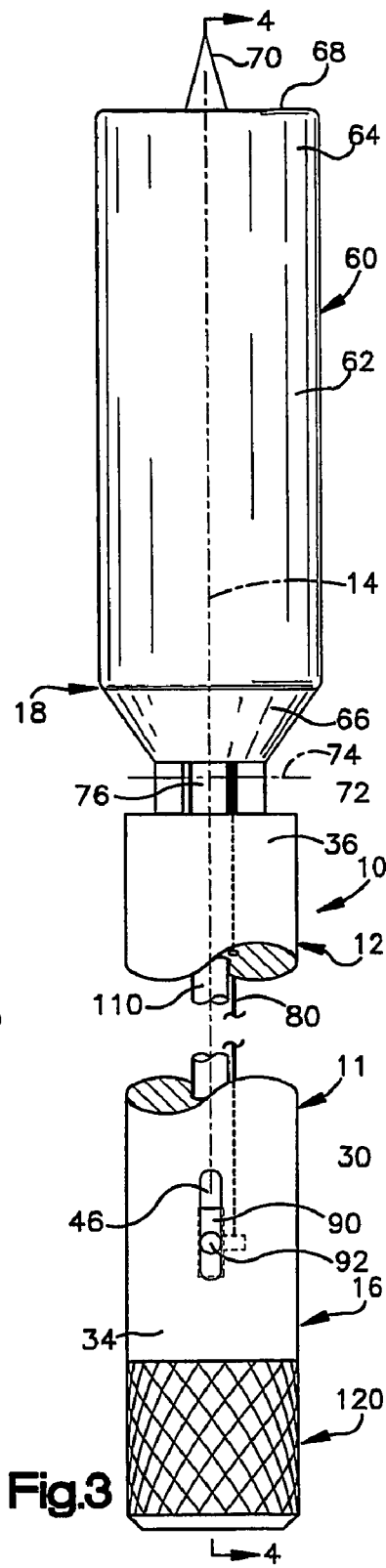

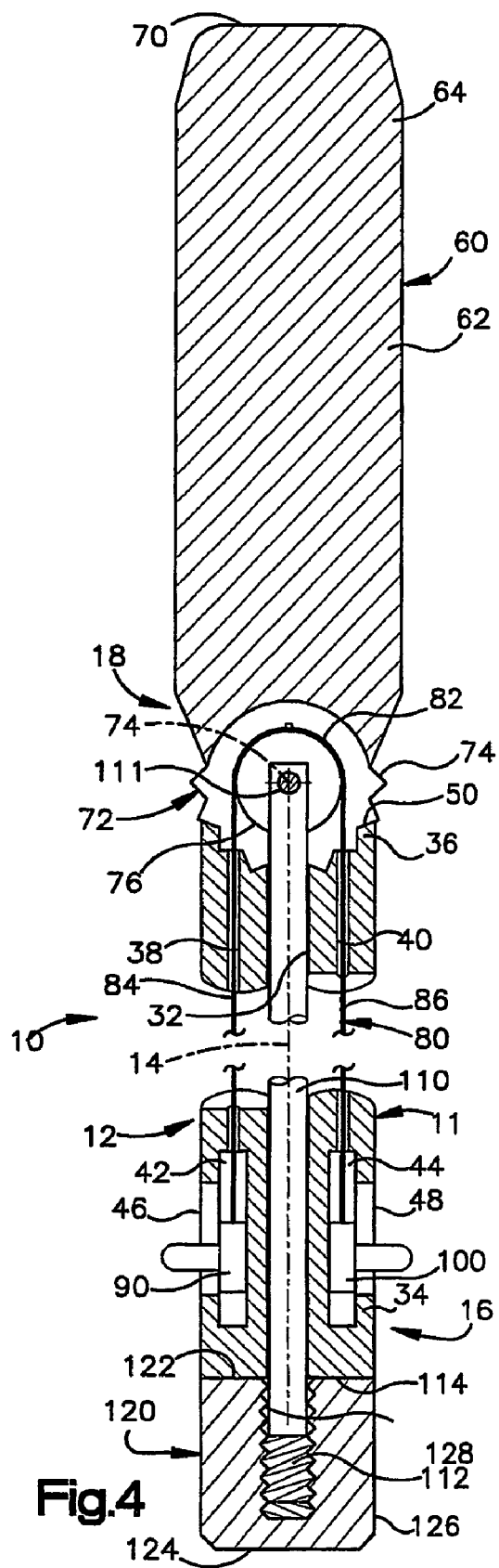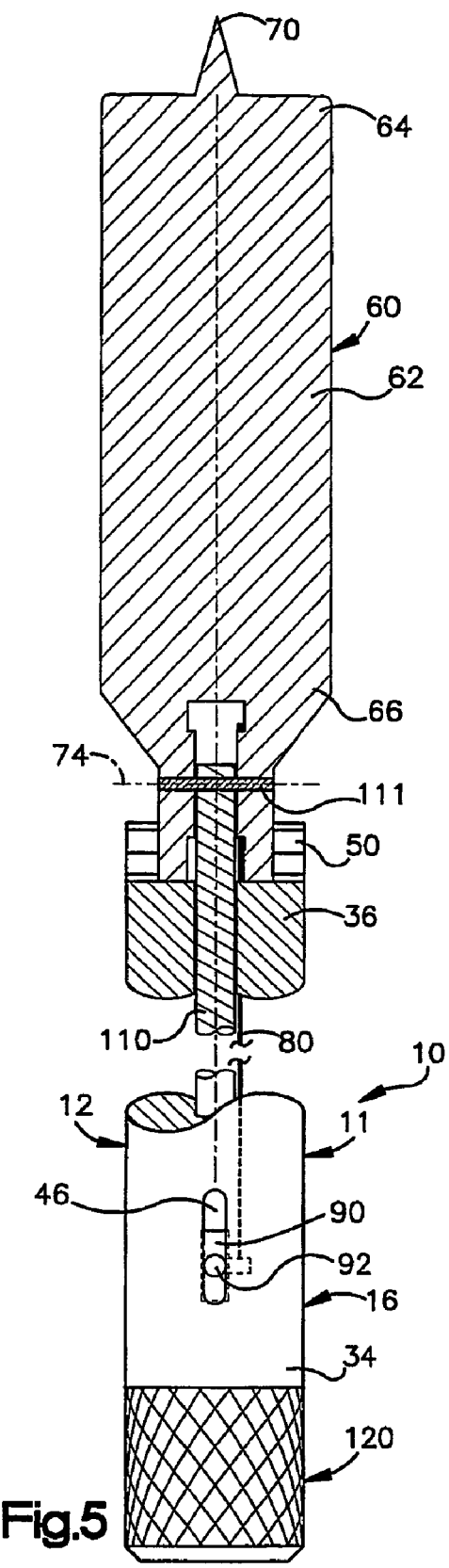

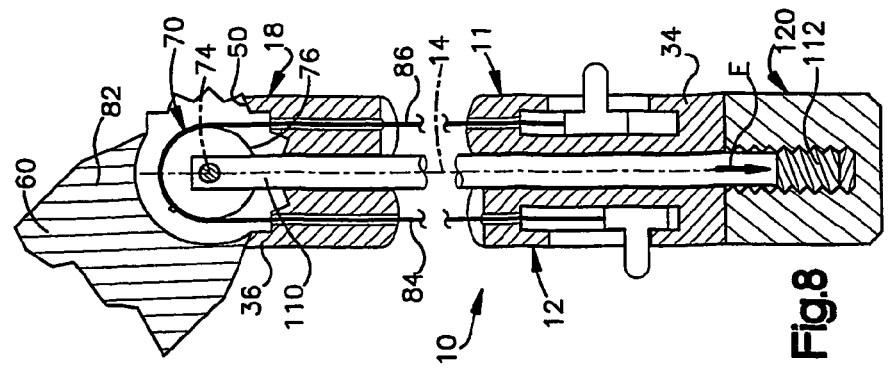
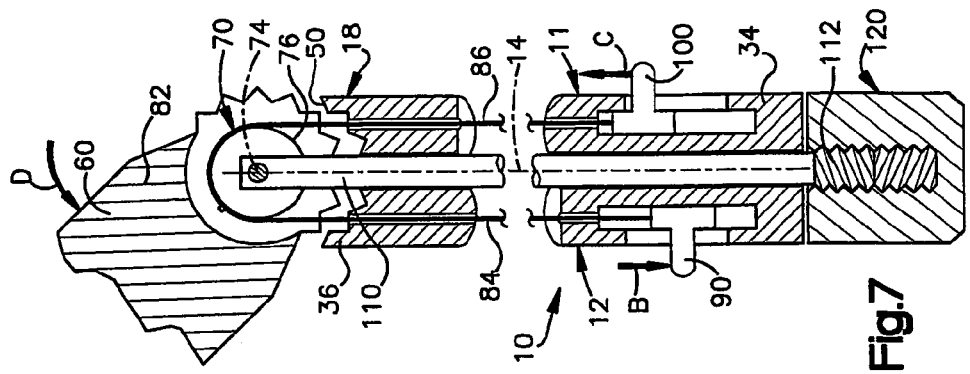
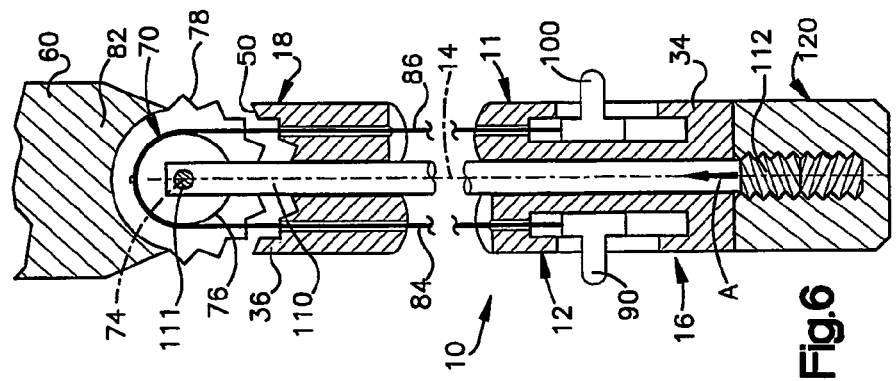

ARTICULATABLE APPARATUS FOR CUTTING BONE

RELATED APPLICATIONS

The present application claims the benefit of U.S. Provisional Patent Application Ser. No. 60/436,867, entitled PERCUTANEOUS CONTROLLED VERTEBRAL OSTEOTOMY TOOL SET, filed Dec. 27, 2002.

TECHNICAL FIELD

The present invention relates to an articulatable apparatus for cutting bone and, in particular, is directed to a uniquely designed osteotome that is useful in cutting vertebrae.

BACKGROUND OF THE INVENTION

A known procedure for treating vertebral compression fractures and other bone-related disorders is vertebral augmentation with bone cement. Vertebral augmentation can be performed by the direct injection of liquid cement into the collapsed vertebral body (commonly known as "vertebroplasty"). Vertebral augmentation can also be performed after the restoration of the vertebrae to near normal vertebral body anatomy and creation of an internal cavity with the use of an inflatable bone tamp. This minimally invasive procedure is commonly known as "kyphoplasty" (see, for example, U.S. Pat. Nos. 4,969,888 and 5,108,404). During the kyphoplasty procedure, the inflatable bone tamp is inserted through a small skin incision which accommodates a working tube passed into the vertebral body. Inflation of the bone tamp compresses the cancellous bone and desirably moves the fractured cortical bone to its pre-fractured orientation, creating a cavity within the vertebral body that can then be filled with a settable material such as a cement or any number of synthetic bone substitutes. In effect, the procedure "sets" the vertebra at or near its pre-fracture position and creates an internal "cast", protecting the vertebra from further fracture and/or collapse.

As compared to a traditional vertebroplasty procedure, kyphoplasty restores the vertebrae to a pre-fractured condition and the injected bone filler is less likely to leak out of the vertebral body during a kyphoplasty procedure. However, under some circumstances, it has been observed that unpredictable reductions can occur with the kyphoplasty technique in chronic or partially healed collapsed vertebral bodies. Under those circumstances, the surgeon would typically resort to a large open operation to re-align the post-traumatic kyphosis. Further, inadequate reductions can occur with certain other spinal deformities such as scoliosis and kyphosis using the known techniques and surgical tools. The large open operations do carry with them significant morbidity in an already physiologically compromised elderly population. The principle benefit of the percutaneous minimally invasive approach, which is the hallmark of the kyphoplasty procedure, is the minimal morbidity associated with the procedure. In this light, additional tools are required to further the technique, achieve better anatomic re-alignment of the spine, and maintain the minimally invasive nature of the surgery. The additional tools will be deployed through small working portals and be able to achieve the desired strategic vertebral osteotomies to move bone in three dimensional space. One such tool would provide a minimally invasive means to safely cut the side (or lateral) wall of a vertebral body, such as a lateral wall with a prior and at least partially healed compression fracture, from within the medullary cavity in the vertebral body. A tool with an articulatable cutting blade is particularly desirable so that aimed strategic osteotomies can be made across a broad path despite working within the confines of the medullary cavity in the vertebral body and the percutaneous cannula.

SUMMARY OF THE INVENTION

The present invention is an apparatus for cutting bone comprising an elongate member having a central axis. The elongate member includes a tubular portion that extends between a proximal end portion and a distal end portion. The distal end portion includes an articulatable head section with at least one stop surface and a cutting edge projecting from the at least one stop surface. The head section is articulatable about a pivot axis that extends transverse to the central axis. The apparatus further includes means for articulating the head section relative to the tubular portion.

The present invention further provides an apparatus for cutting through cortical bone in a vertebral body. The apparatus comprises an elongate member having a central axis. The elongate member includes a tubular portion that extends between a proximal end portion and a distal end portion. The distal end portion includes an articulatable head section with a cutting edge for cutting cortical bone and at least one stop surface for engaging the cortical bone after the cortical bone is cut by the cutting edge to stop further movement of the head section and prevent the cutting edge from undesirably engaging other tissue or bone. The head section of the distal end portion is pivotable between a plurality of predetermined angular positions about a pivot axis that extends transverse to the central axis. The apparatus further comprises a mechanism for pivoting the head section relative to the tubular portion.

The present invention further provides a minimally invasive method for cutting through cortical bone in a vertebral body. In accordance with the inventive method, an elongate member having a central axis is provided. The elongate member includes a tubular portion that extends between a proximal end portion and a distal end portion. The distal end portion includes an articulatable head section with a cutting edge for cutting cortical bone. The head section is controllably pivotable between a plurality of predetermined angular positions about a pivot axis that extends transverse to the central axis. A cannula is placed through a pedicle of the vertebral body. The distal end portion of the elongate member is inserted into the cancellous bone in the vertebral through the cannula. The proximal end portion of the elongate member is then tapped on, by hand or hammer, to advance the elongate member and cut a first portion of the peripheral wall of the vertebral body with the cutting edge. The at least one stop surface engages the cortical bone after the cortical bone is cut by the cutting edge to stop further movement of the head section and prevent the cutting edge from undesirably engaging other tissue or bone. The head section is then pivoted to a different angular position while the distal end portion is located within the vertebral body. The proximal end portion of the elongate member is again manually impacted to advance the elongate member and cut a second portion of the peripheral wall of the vertebral body with the cutting edge.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a view of an articulatable apparatus for cutting bone constructed in accordance with the present invention;

FIG. 2 is a view taken along line 2-2 in FIG. 1;

FIG. 3 is a view taken along line 3-3 in FIG. 1;

FIG. 4 is a sectional view taken along line 4-4 in FIG. 3;

FIG. 5 is a sectional view taken along line 5-5 in FIG. 1;

FIG. 6 is a sectional view similar to FIG. 4 with an end portion of the apparatus in an axially displaced position;

FIG. 7 is a sectional view similar to FIG. 6 with the end portion of the apparatus in an angularly displaced position;

FIG. 8 is a sectional view similar to FIG. 7 with the end portion of the apparatus returned to its original axial position;

DESCRIPTION OF EMBODIMENTS

Figure 9:
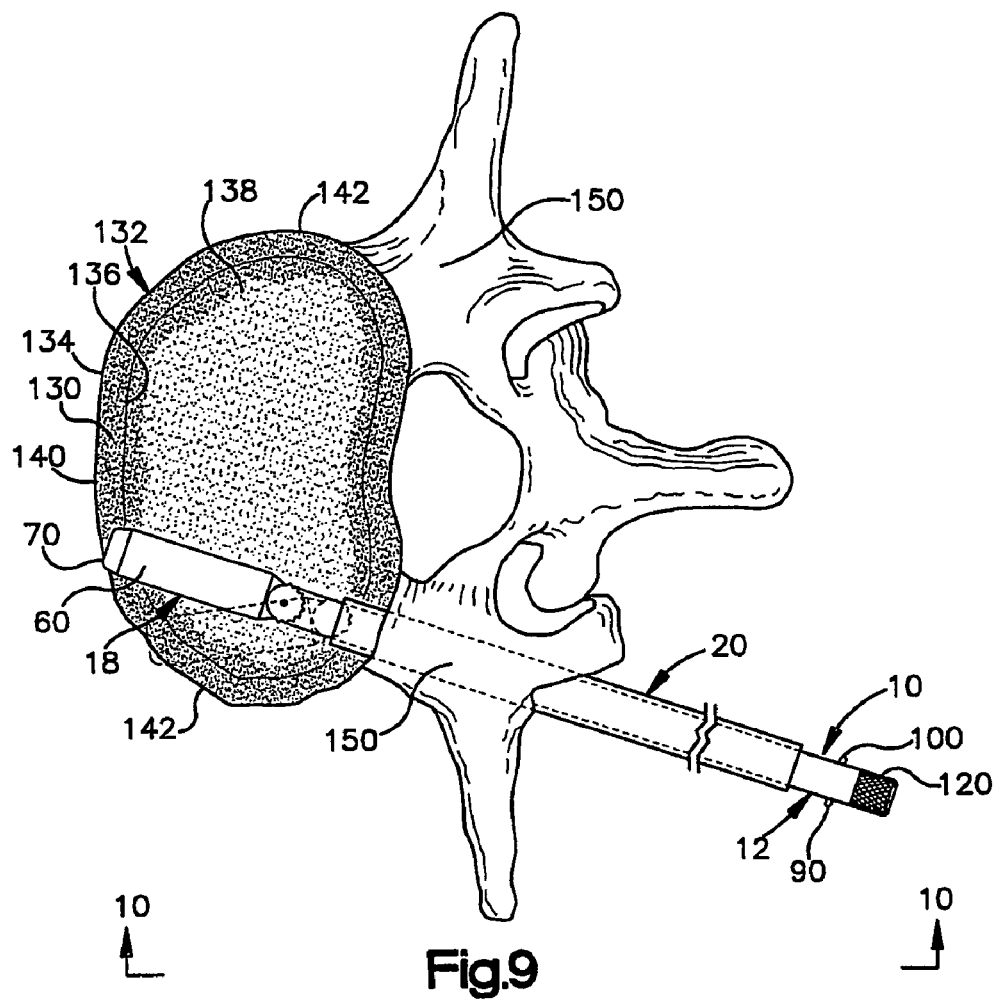
FIG. 9 is a plan view illustrating the apparatus of FIG. 1 being used to cut through cortical bone in a vertebral body.

The present invention relates to an articulatable apparatus for cutting bone and, in particular, is directed to a uniquely designed osteotome that is useful in cutting cortical bone in vertebrae. As representative of the present invention, FIG. 1 illustrates an apparatus 10 comprising an elongate member 11 made of a medical grade metal such as stainless steel. The elongate member 11 includes a tubular portion 12 extending along a central axis 14 between a proximal end portion 16 and a distal end portion 18 of the apparatus 10. The apparatus 10, in particular the tubular portion 12 and the distal end portion 18, are designed to fit through a 5 mm (inner diameter) cannula 20 (FIG. 9) and thus have a maximum outer diameter of 4.8 mm. It should, however, be understood that the apparatus 10 and the cannula 20 could have correspondingly larger or smaller diameters.

The tubular portion 12 of the apparatus 10 includes a cylindrical outer surface 30 and a central passage 32 (FIG. 4) that extends along the axis 14 between a proximal end 34 and a distal end 36. The tubular portion 12 further includes parallel first and second passages 38 and 40 that extend on opposite sides of the central passage 32. The first passage 38 extends from the distal end 36 of the tubular portion 12 to a first slot 42 near the proximal end 34. Similarly, the second passage 40 extends from the distal end 36 of the tubular portion 12 to a second slot 44 near the proximal end 34. The first and second slots 42 and 44 in the tubular portion 12 extend from the first and second passages 38 and 40, respectively, to oppositely disposed first and second openings 46 and 48, respectively, in the cylindrical outer surface 30. As best seen in FIG. 6, the distal end 36 of the tubular portion 12 includes a set of ratchet teeth 50 that extend in a concave manner along a hemispherical arc.

The distal end portion 36 of the apparatus 10 includes an articulatable head section 60 (FIG. 1) having a main body portion 62 extending between oppositely disposed first and second ends 64 and 66. The cross-sectional shape of the head section 60 may be circular, oval, rectangular or other suitable shape. The first end 64 of the head section 60 has a planar stop surface 68 (FIG. 2) that is perpendicular to the central axis 14. A cutting edge 70 projects axially at a right angle from the stop surface 68. In the illustrated embodiment, the cutting edge 70 is a smooth blade, however it is contemplated that the cutting edge could be serrated or spiked to produce perforations instead of osteotomies.

The second end 66 of the head section 60 includes a ratchet wheel 72 fixed to the head section 60. The ratchet wheel 72 has a pivot axis 74 that extends perpendicular to the central axis 14. The head section 60 is pivotable about the pivot axis 74. The ratchet wheel 72 includes a centrally located cylindrical section 76 (FIG. 4) and a set of ratchet teeth 78 that extend in a convex manner along a hemispherical arc. The set of ratchet teeth 78 on the ratchet wheel 72 are complementary to, and adapted for meshing engagement with, the set of ratchet-teeth 50 on the distal end 36 of the tubular portion 12.

The apparatus 10 further includes a wire member 80 and first and second levers 90 and 100. The wire member 80 is operatively coupled to the ratchet wheel 72 and includes a middle portion 82 and oppositely disposed first and second ends 84 and 86. The middle portion 82 of the wire member 80 is fixedly attached to the cylindrical section 76 of the ratchet wheel 72. The first and second ends 84 and 86 of the wire member 80 extend in parallel into the first and second passages 38 and 40, respectively, in the tubular member 12 and are attached to the first and second levers 90 and 100, respectively.

The first and second levers 90 and 100 are housed and supported for relative axial movement within the first and second slots 42 and 44, respectively, in the tubular portion 12 of the elongate member 11. The first lever 90 includes a manually engageable flange 92 that projects radially outward through the first opening 46 in the tubular member 12. Similarly, the second lever 100 includes a manually engageable flange 102 that projects radially outward through the second opening 48 in the tubular member 12.

The apparatus 10 also includes a shaft member 110 and a cap member 120. One end of the shaft member 110 is attached to the head section 60 by a pin 111 at the pivot axis 74 so that the head section can pivot relative to the shaft member. The shaft member 110 extends into the central passage 32 in the tubular member 12 and is axially movable within the central passage. The opposite end of the shaft member 110 includes an external threaded portion 112 (FIG. 4) that projects axially beyond an end 114 surface at the proximal end portion 34 of the tubular member 12.

The cap member 120 includes oppositely disposed first and second end surfaces 122 and 124 and cylindrical inner and outer surfaces 126 and 128. The first end surface 122 faces toward and is engageable with the end surface 114 at the proximal end 34 of the tubular member 12. The second end surface 124 of the cap member 120 is adapted to receive repetitive impacts. The outer surface 126 of the cap member is knurled (see FIG. 1), while the inner surface 128 is threaded to mate with the threaded portion 112 of the shaft member 110.

As illustrated in FIGS. 6-8, the head section 60 of the apparatus 10 can be articulated from the position of FIG. 4 to a number of predetermined angular positions (based on the number of ratchet teeth 50 and 78) to change the direction of the cutting edge 70. The head section 60 is articulated by first unscrewing the cap member 120 from the end 112 of the shaft member 110, which permits axial movement of the shaft member in the direction of arrow A in FIG. 6. The slotted openings 46 and 48 in the tubular member 12 allow for limited axial movement of the levers 90 and 100. This axial movement of the shaft member 110 moves the ratchet teeth 78 on the ratchet wheel 72 out of engagement with the ratchet teeth 50 on the tubular member 12.

The head section 60 of the apparatus 10 is then pivoted about the pivot axis 74 by manually moving the first and second levers 90 and 100 in opposite axial directions, as shown by arrows B and C in FIG. 7. This relative axial movement of the first and second levers 90 and 100 causes the wire member 80 to rotate the ratchet wheel 72 about the pivot axis 74 as shown by arrow D in FIG. 7. It is contemplated that calibrated markings can be placed near the openings 46 and 48 in the tubular member 12 to indicate the amount of rotation of the head section 60 that results from a given amount of axial movement of the levers 90 and 100.

Once a desired amount of rotation is achieved (i.e. the cutting edge 70 is pointed in a desired direction), the cap member 120 is re-tightened on the end 112 of the shaft member 110, which moves the shaft member in the direction of arrow E in FIG. 8. This axial movement of the shaft member 110 pulls the ratchet teeth 50 and 78, respectively, into engagement and locks the head section 60 in the desired angular position.

Figure 10:
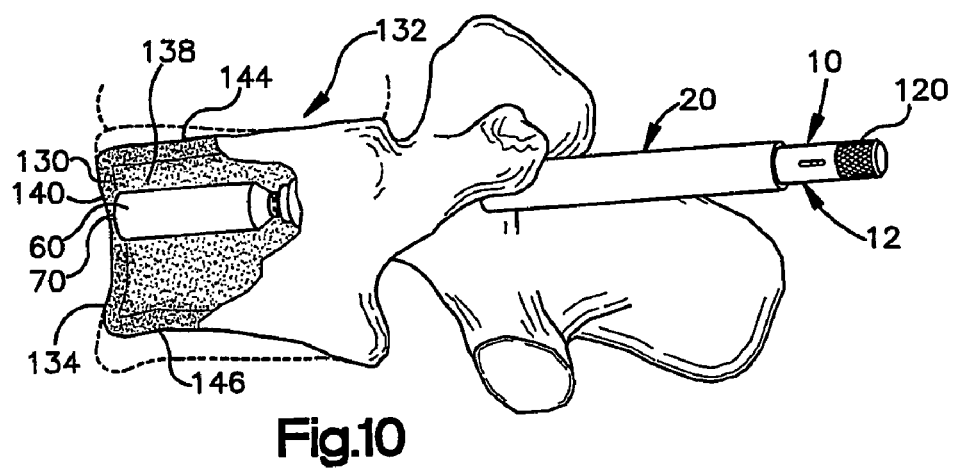
FIG. 10 is a side view taken along line 10-10 in FIG. 9.

FIGS. 9 and 10 illustrate use of the apparatus 10 to cut bone. Specifically, FIGS. 9 and 10 illustrate the apparatus 10 cutting through cortical bone 130 of a vertebral body 132. The cortical bone 130 has an outer peripheral surface 134 and an inner surface 136 surrounding cancellous bone 138. As best seen in FIG. 10, the vertebral body 132 has a partially healed compression fracture to be treated via a kyphoplasty procedure. In order to perform the kyphoplasty procedure, the partially healed cortical bone 130 in the anterior wall 140 and the lateral wall 142 of the vertebral body 132 must be cut to release the upper and lower end plates 144 and 146 of the vertebral body so that an inflatable bone tamp (not shown) inserted inside the vertebral body can, when inflated, move the upper and/or lower end plates back to their pre-fractured positions (illustrated in dashed lines).

Access into the vertebral body 132 occurs in a minimally invasive manner via the cannula 20. After creating a passage (not numbered) through a pedicle 150 of the vertebral body 132 and into the cancellous bone 138 via a drilling or reaming procedure, the cannula 20 is placed through the pedicle as shown in FIG. 9. The distal end portion 18 of the apparatus 10 is then inserted through the cannula 20 and into the cancellous bone 138 of the vertebral body. The cutting edge 70 on the head section 60 is then advanced through the cancellous bone 138 and into engagement with the cortical bone 130 of the anterior wall 140. The apparatus 10 is advanced, via impact blows either by hand or by hammer (not shown) to the surface 124 on the cap member 120, so that the cutting edge 70 itself creates a "pathway" through the cancellous bone 138 to the anterior wall 140. Alternatively, another tool (not shown) may be used to create the aforementioned pathway through the cancellous bone 138 prior to the insertion of the apparatus 10 into the cannula 20.

Next, the cutting edge 70 is tapped through the cortical bone 130 of the anterior wall 140 of the vertebral body 132 through impact blows, either by hand or by hammer, to the cap member 120. As the cutting edge 70 cuts through the anterior wall 140, axial movement of the cutting edge is stopped when the stop surface 68 on the head section 60 engages the inner surface 136 of the cortical bone 130. This prevents the cutting edge 70 from undesirably straying beyond the vertebral body 132 and cutting other tissues, such as blood vessels, nerves, and muscles, or bones.

In order to fully release the end plates 144 and 146 of the vertebral body 132, it is likely that additional cuts through the anterior wall 140 and through adjoining portions of the lateral walls 142 will be needed. The articulatable apparatus 10 is uniquely adapted to make these additional cuts by changing the angular position of the head section 60 (and thus the cutting edge 70), as shown schematically by the dashed lines in FIG. 9. Through a systematic adjustment of the angle of the cutting edge 70 and ensuing cuts through the anterior wall 140 and/or lateral wall 142, the cortical bone 130 around the periphery of the vertebral body 132 can be sufficiently severed to release the end plates 144 and 146 for a kyphoplasty procedure. Thus, the apparatus 10 described above permits aimed strategic osteotomies along the periphery of a vertebral body 132 in a safe manner so that a minimally invasive kyphoplasty procedure can be used to treat the compression fracture of the vertebral body.

From the above description of the invention, those skilled in the art will perceive improvements, changes and modifications. For example, it should be understood that, depending on the nature of the condition of a given vertebral body, the anterior and lateral walls nearer the opposite side of the vertebral body 132 shown in FIG. 9, or on both sides of the vertebral body, may need to be cut in order to release the end plates 144 and 146 of the vertebrae. In such situations, the apparatus 10 would be used in an identical fashion with access through a cannula placed through the other pedicle. Further, it should be understood that the apparatus 10 disclosed herein could be used to cut through other areas of cortical bone in vertebrae, as well as cortical bone in other bones in a mammalian body. Such improvements, changes and modifications within the skill of the art are intended to be covered by the appended claims.

Having described the invention, I claim:

1. An apparatus for cutting bone, said apparatus comprising:

an elongate member having a central axis, said elongate member including a tubular portion that extends between a proximal end portion and a distal end portion, said distal end portion including an articulatable head section having a first end and a second end, said second end terminating with at least one planar stop surface, a cutting edge projects from, and is integrally formed with, said at least one planar stop surface, the remainder of said at least one planar stop surface limiting movement of said cutting edge along the central axis, said head section being articulatable about a pivot axis that extends transverse to said central axis; and means for articulating said head section relative to said tubular portion.

2. The apparatus of claim 1 further comprising a shaft member connected to said head section and extending coaxially within said tubular portion, said shaft member and said head section being longitudinally movable relative to said tubular portion.

3. The apparatus of claim 2 wherein said shaft member includes a terminal end portion that projects beyond said proximal end portion of said elongate member.

4. The apparatus of claim 3 further comprising a cap member that is removably attached to said terminal end portion of said shaft member, said cap member including a first surface that is engageable with said proximal end portion of said elongate member and an oppositely disposed second surface adapted to receive repetitive impacts.

5. The apparatus of claim 1 wherein said cutting edge projects from the at least one planar stop surface a predetermined height, the remainder of said at least one planar stop surface limiting movement of said cutting edge along the central axis to the predetermined height.

6. The apparatus of claim 1 wherein the cutting edge extends along a midline of the at least one planar stop surface.

7. A minimally invasive method for cutting through cortical bone in a vertebral body, said method comprising the steps of:

providing an elongate member having a central axis, the elongate member including a tubular portion that extends between a proximal end portion and a distal end portion, the distal end portion including an articulatable head section with a cutting edge for cutting cortical bone, the head section being controllably pivotable between a plurality of predetermined angular positions about a pivot axis that extends transverse to the central axis;

placing a cannula through a pedicle of the vertebral body;
inserting the distal end portion of the elongate member into the cancellous bone in the vertebral through the cannula;
tapping on the proximal end portion of the elongate member to advance the elongate member and cut a first portion of the peripheral wall of the vertebral body with the cutting edge, the at least one stop surface engaging the cortical bone after the cortical bone is cut by the cutting edge to stop further movement of the head section and prevent the cutting edge from undesirably engaging other tissue or bone;
pivoting the head section to a different angular position while the distal end portion is located within the vertebral body; and
tapping on the proximal end portion of the elongate member to advance the elongate member and cut a second portion of the peripheral wall of the vertebral body with the cutting edge.

8. The method of claim 7 wherein said step of pivoting the head section includes manually moving a mechanism for pivoting the head section relative to the tubular portion, the mechanism being at least partially located at the proximal end portion of the elongate member.

9. An apparatus for cutting bone, said apparatus comprising:
an elongate member having a central axis, said elongate member including a tubular portion that extends between a proximal end portion and a distal end portion, said distal end portion including an articulatable head section having a first end and a second end, said second end terminating with at least one planar stop surface, a cutting edge is integrally formed with said at least one planar stop surface and projects from the at least one planar stop surface a predetermined height, the remainder of said at least one planar stop surface limiting axial movement of said cutting edge along the central axis to the predetermined height, said head section being articulatable about a pivot axis that extends transverse to said central axis, wherein said distal end portion of said elongate member further includes a ratchet wheel fixed to said head section for pivotal movement about said pivot axis, said ratchet wheel having a first set of ratchet teeth, said first set of ratchet teeth being engageable with a complimentary second set of ratchet teeth on a distal end of said tubular portion; and
means for articulating said head section relative to said tubular portion,
wherein said means for articulating said head section includes a wire member operatively coupled to said ratchet wheel and having first and second ends extending into said tubular portion, said first and second ends of said wire member being attached to respective first and second levers disposed in said distal end portion of said elongate member, said first and second levers being manually engageable and axially movable relative to each other to cause rotation of said head section about said pivot axis.

10. An apparatus for cutting bone, said apparatus comprising:
an elongate member having a central axis, said elongate member including a tubular portion that extends between a proximal end portion and a distal end portion, said distal end portion including an articulatable head section having a first end and a second end, said second end terminating with at least one planar stop surface, a cutting edge is integrally formed with, and extends along a midline of, said at least one planar stop surface, wherein said cutting edge projects a predetermined height from said at least one planar stop surface to cut the bone, said at least one planar stop surface engaging the bone after the bone is cut by said cutting edge to prevent said cutting edge from cutting the bone a depth greater than the predetermined height to prevent said cutting edge from undesirably engaging other tissue or bone, said head section being articulatable about a pivot axis that extends transverse to said central axis; and
means for articulating said head section relative to said tubular portion.

11. An apparatus for cutting through cortical bone in a vertebral body, said apparatus comprising:
an elongate member having a central axis, said elongate member including a tubular portion that extends between a proximal end portion and a distal end portion;
said distal end portion including an articulatable head section having a first end and a second end, said second end terminating with at least one planar stop surface, a cutting edge for cutting cortical bone projects from, and is integrally formed with, said at least one planar stop surface, said at least one planar stop surface engages the cortical bone after the cortical bone is cut by said cutting edge to stop further movement of said head section and prevent said cutting edge from undesirably engaging other tissue or bone;
said head section of said distal end portion being pivotable between a plurality of predetermined angular positions about a pivot axis that extends transverse to said central axis, wherein said distal end portion of said elongate member includes a ratchet wheel fixed to said first end of said head section for pivotal movement about said pivot axis, said ratchet wheel having a first set of ratchet teeth, said first set of ratchet teeth being engageable with a complimentary second set of ratchet teeth on said distal end of said tubular portion; and
a mechanism for pivoting said head section relative to said tubular portion,
wherein said mechanism for pivoting said head section includes a wire member operatively coupled to said ratchet wheel and having first and second ends extending into said tubular member, said first and second ends of said wire member being attached to respective first and second levers disposed in said distal end portion of said elongate member, said first and second levers being manually engageable and axially movable relative to each other to cause rotation of said head section about said pivot axis.

12. The apparatus of claim 11 further comprising a shaft member connected to said articulatable head section and extending coaxially within said tubular portion, said shaft member and said articulatable head section being axially movable relative to said tubular portion to permit engagement and disengagement of said first and second sets of ratchet teeth.

13. The apparatus of claim 12 wherein said shaft member includes a threaded end portion that projects beyond said proximal end portion of said elongate member.

14. The apparatus of claim 13 further comprising a threaded cap member that is removably attachable to said terminal end portion of said shaft member to releasably lock said head section in a desired angular position relative to said tubular portion.

15. The apparatus of claim 14 wherein said threaded cap member includes a first surface that is engageable with said proximal end portion of said elongate member and an oppositely disposed second surface adapted to receive repetitive impacts.

* * * * *